United States Patent [19]

Scott

[11] 4,357,143

[45] Nov. 2, 1982

[54] DETERMINING ION CONCENTRATION

[75] Inventor: Richard L. Scott, Bartlesville, Okla.

[73] Assignee: Phillips Petroleum Company, Bartlesville, Okla.

[21] Appl. No.: 197,875

[22] Filed: Oct. 17, 1980

Related U.S. Application Data

[63] Continuation-in-part of Ser. No. 75,392, Sep. 14, 1979, abandoned.

[51] Int. Cl.³ .............................................. G01N 27/46
[52] U.S. Cl. .................................. 23/230 R; 204/1 T; 204/195 G; 204/195 M; 204/195 R; 210/662; 210/96.1; 422/68
[58] Field of Search ........................ 23/230 R; 422/68; 210/662, 96.1; 204/1 T, 1 B, 1 N, 1 K, 1 F, 1 A, 1 H, 195 R, 195 M, 195 G

[56] References Cited

U.S. PATENT DOCUMENTS

| | | | |
|---|---|---|---|
| 2,628,194 | 2/1953 | Gilwood | 210/662 |
| 2,880,071 | 3/1959 | Gelman | 23/230 R |
| 3,296,113 | 1/1967 | Hansen | 204/195 R |
| 3,591,481 | 7/1971 | Riseman | 204/195 R |
| 3,839,162 | 10/1974 | Ammer | 204/195 M |
| 3,856,633 | 12/1974 | Fletcher | 204/195 M |
| 3,865,708 | 2/1975 | Light et al. | 204/195 M |
| 4,002,428 | 1/1977 | Blanchard | 23/230 R |

Primary Examiner—Kenneth M. Schor

[57] ABSTRACT

A method for determining the concentration of a specific ion in a solution which involves dividing the solution to be analyzed into two portions. One portion is treated with an ion exchange resin with the other portion being treted with a reagent, e.g., a precipitating agent in order to remove the desired ion from solution, and at least one ion exchange resin. The reagent and ion exchange resin can be one and the same. The two streams are then passed into opposite sides of a detection cell comprising two ion specific electrodes connected through conventional bridge circuitry. The concentration of the desired ion is determined from the difference in electrical potential between the two ion specific electrodes. Instead of dividing the stream and then treating the reference portion it is also possible to treat the entire stream first to replace all ions changed oppositely to the desired ions and then divide the streams.

36 Claims, 1 Drawing Figure

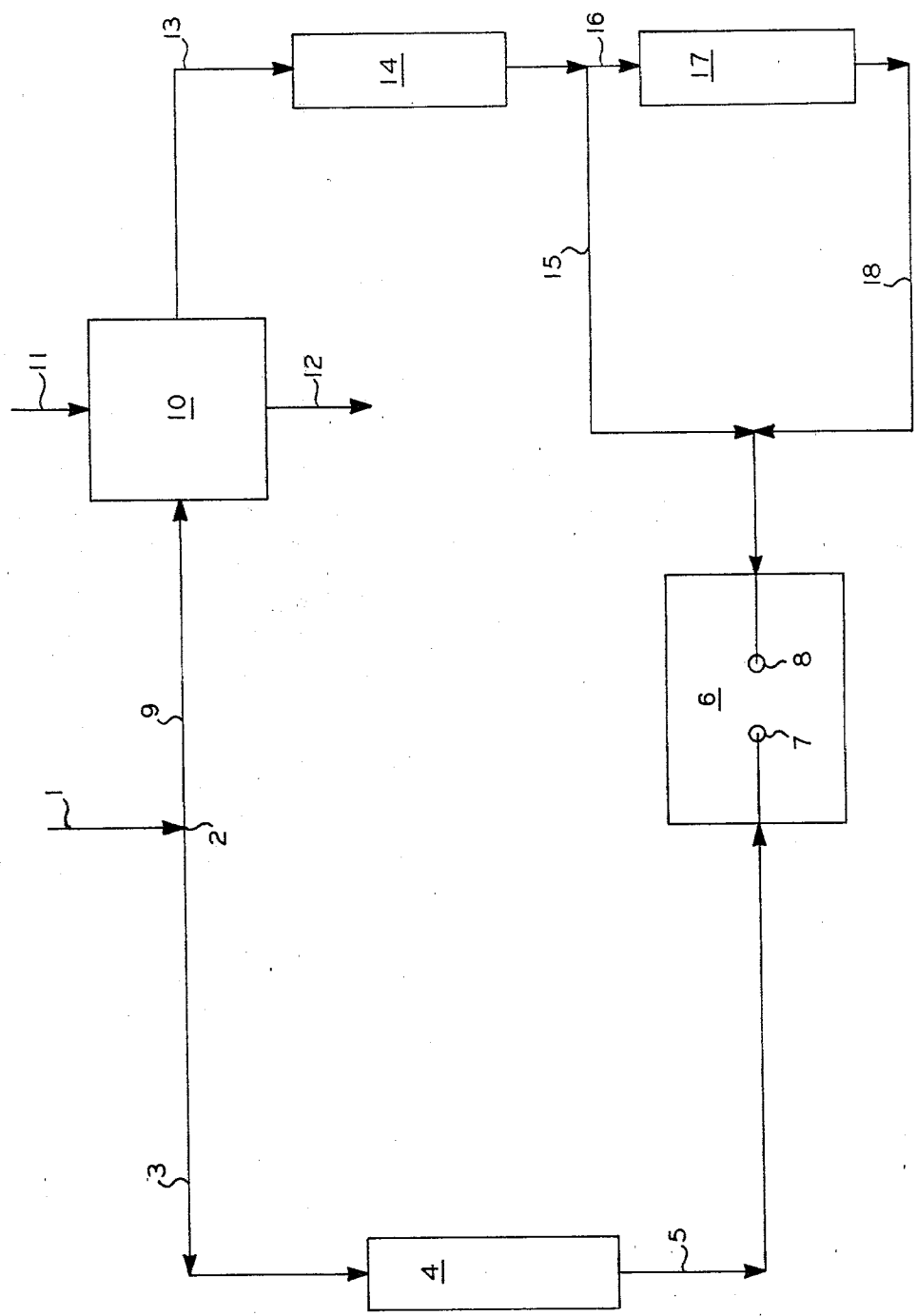

DETERMINING ION CONCENTRATION

This application is a continuation-in-part of Ser. No. 075,392, filed Sept. 14, 1979 now abandoned.

The present invention relates to a method for determining the concentration of specific ions in solution. In another aspect, this invention relates to a method for determining an ion concentration in solution which employs ion exchange resins to exchange all anionic or cationic species for a single anionic or cationic species. In another aspect, this invention relates to a method for determining an ion concentration which employs ion specific electrodes which are specific to the ionic species obtained from employing ion exchange resins. In still another aspect, this invention relates to a method for determining the concentration of a desired ion which employs two ion specific electrodes connected through a bridge circuit. Still another aspect of this invention relates to a method for determining the concentration of the desired ion wherein the desired ion is removed from solution by precipitation or formation of non-ionic products. Another aspect of this invention relates to an apparatus which is useful in determining the concentration of a specific ion in solution. This invention also relates to an apparatus comprising at least two ion exchange zones and two ion specific electrodes connected through a bridge circuit.

BACKGROUND OF THE INVENTION

A number of methods are known in the art for measuring the concentration of specific ions in solution. One method involves introducing a reagent into a sample solution to thereby form a precipitate with the ion whose concentration is to be measured. The precipitate is separated from the solution, dried, weighed, and then the amount of the ion is calculated based on the amount of precipitate formed. This method is cumbersome and time consuming, however, and requires essentially non-portable equipment such as an accurage weighing apparatus.

Another method is illustrated in U.S. Pat. No. 2,880,071, issued Mar. 31, 1959 to Gelman. The method employed comprises measuring the conductivity of the solution. U.S. Pat. No. 4,002,428, issued Jan. 11, 1977 to Blanchard, also employs conductivity measurements as well as pH measurements and the addition of a reagent capable of reacting with the desired ion to get a substantially non-ionic product. Briefly, the process disclosed in U.S. Pat. No. 4,002,428 comprises first measuring the pH and specific conductivity of the sample solution and of a reagent solution. The process then adds and reacts the measured excess amount of the reagent solution with the sample solution thereby allowing the reagent solution to react with the desired ion to get a substantially non-ionic product without a substantial reaction taking place between the reagent solution and the other ions in the solution. The pH and specific conductivity of the resultant mixture is then measured and the concentration of the desired ion mathematically deduced by comparing the specific conductivity expected in the mixture of the sample solution and the reagent solution, assuming no reaction had taken place, with the measured specific conductivity for the solution obtained upon mixing the two solutions and by making any necessary corrections for pH changes and for the solubility of the product of reaction between the desired ion and the reagent solution. Such methods can be somewhat time consuming and are only really applicable in a batch-type method upon taking a sample of the solution to be measured.

Another method is disclosed in U.S. Pat. No. 3,591,481, issued July 6, 1971 to Riseman. The method employs an ion specific electrode. In this method concentration measurements are effected by relating the electrode potential resulting from an unknown or sample solution with the electrode potential from a mixture of that sample solution with a standard solution of known concentration of the ion of interest or a strong complexing or precipitating agent for the ion of interest. The method of obtaining a measurement requires two essential steps. First, the electrode sensitive to the ion of interest is immersed into a specific volume (e.g., 50 ml) of the sample solution containing an unknown amount of the ion of interest; the potential developed then causes a deflection of a meter movement in accordance with the Nernst equation. The meter movement is then adjusted to a null point and small known volume (e.g., 1 ml) of a standard solution containing a known concentration of the ion of interest (or a strong complexing or precipitating agent therefor) is added to the sample. The addition of the standard solution will change the total so that a new potential will arise which causes the meter movement to deflect away from the null point by some value $\Delta E$. Since the concentration of the standard solution is predetermined, the concentration of the sample will appear as a reading on the meter scale or base expressed typically in moles per liter based on the value of $\Delta E$.

The method of the present invention, however, provides an alternative method for measuring the concentration of the specific ion in solution which employs ion exchange resins as well as ion specific electrodes. The present invention exhibits advantages over current analysis methods in that the method is suitable for use in continuous flow systems, is more sensitive than currently available methods, and is more rapid than current methods.

Accordingly, it is an object of this invention to provide a novel process and apparatus for determining the concentration of an ion in solution.

Another object of this invention is to provide a method for determining the concentration of an ion in solution which is suitable for use in continuous flow systems.

Still another object of this invention is to provide a method which is more sensitive and more rapid than currently available methods for determining the concentration of an ion in solution.

Other aspects, objects, and advantages of the present invention will become apparent from a study of the disclosure, the appended claims, and the drawing.

BRIEF DESCRIPTION OF THE DRAWING

The FIGURE shows a schematic diagram of the apparatus and process of this invention.

SUMMARY OF THE INVENTION

In accordance with this invention a method for determining the concentration of desired ions in a solution is provided for. The term "desired" refers only to the goal of the analysis, not to the fact whether these ions are advantageous or detrimental to the process from which the sample solution originates. This method is characterized by generating two streams from the solution to be measured. A first stream, or measurement stream, is generated which contains only ions of one charge to which a measurement electrode is sensitive and which contains these ions in a concentration which is equivalent to the difference between the original ion concentration of that charge minus the concentration of the desired ions. Whenever concentrations are mentioned in this context, it is to be understood that the equivalent concentrations are meant, i.e., that in the case of multivalent ions the actual concentrations of these ions have to be multiplied by the number of charges that these ions are carrying. A second stream, or reference stream, is generated which contains only those ions of one charge to which a reference electrode is sensitive, equivalent in concentration to the original ion concentration of the solution. In other words the present invention involves a measurement electrode and a reference electrode sensitive preferably to ions of the same charge, wherein the reference electrode "sees" a liquid with ions to which the reference electrode is sensitive in a concentration equivalent to the original solution concentration whereas the measurement electrode "sees" a solution with ions to which the measurement electrode is sensitive in a concentration equivalent to the difference between the original ion concentration in the solution and the concentration of the desired ions.

The measurement stream can be generated by two different approaches. The first approach resides in a precipitation step followed by at least one ion exchange step. In the precipitation step the desired ions are combined with ions of the opposite charge of a treating agent to form a nonionic product. This treating agent is used in a quantity in excess of the desired ions. Thereby a stream is produced which contains an ionic concentration that is equivalent to the original ionic concentration of the solution minus the concentration of the desired ions plus the concentration of any excess ions of the treating agent. This stream is then ion exchanged so that the excess ions of the treating agent of one charge are replaced by an equivalent amount of other ions which combine with the excess ions of the treating agent of the other charge to form nonionic products such as water. By this step a stream is generated which contains an ionic concentration that is equal to the original ionic concentration of the solution minus the concentration of the desired ion. This stream optionally after another ion exchange step can be used as the measurement stream.

The second possibility of generating the measurement stream resides in two consecutive ion exchange steps. In the first ion exchange step the ions with opposite charge to that of the desired ions are exchanged for a single ionic species which is capable of combining with the desired ions (and only with those) to form a nonionic product (e.g., a precipitate). The resulting stream has an ion concentration equivalent to the difference of the original ion concentration and the concentration of the desired ions. The resulting solution of this ion exchange step can be treated with another ion exchange resin to result in the measurement stream containing among the ions of one charge only those to which the measurement electrode is sensitive and in a concentration equivalent to the difference of concentrations mentioned above.

The reference stream is generated by an ion exchange operation replacing all ions of one charge by ions to which the reference electrode is sensitive, leaving, however, the concentration of these ions equivalent to the concentration of the original solution. This can be done by either carrying out the ion exchange step prior to the splitting of the solution to be measured into two streams or by first splitting the solution to be measured into a measurement and a reference stream and then treating only the reference stream by the ion exchange resin described.

This invention pertains to a method of determining the concentration of a specific ion in a solution wherein the solution to be analyzed is divided into two portions. One portion (reference) is treated with an ion exchange resin to exchange all ionic species for a single ionic species. The other portion (sample) of the solution is treated with a reagent capable of reacting with the desired ionic species to give a substantially non-ionic product without substantial reaction with other ions in the solution. The reagent treated solution is then treated with a second ion exchange resin to exchange all remaining ionic species with a charge opposite to the desired ion for a single ionic species. The two streams are then passed to a detection cell comprising two ion specific electrodes connected through conventional bridging circuitry. Each stream is passed in contact with one of the ion specific electrodes. The measured difference in concentration of ionic species in the treated reference portion of the solution compared to the treated sample portion of the solution represents the concentration of the desired ionic species in the original solution.

In one embodiment of this invention, the reagent is a precipitation agent which results in the precipitation of all the desired species from the solution.

In another embodiment of this invention, the reagent is an ion exchange resin which exchanges the ionic species in the solution with a charge opposite to that of the desired ion for a single ionic species which is capable of combining with the desired ionic species to form a precipitate. The amount of ionic species exchanged by the ion exchange resin need only be an amount sufficient to insure the precipitation of all the desired ionic species from the solution. After the precipitation step, a subsequent ion exchange resin can be employed to exchange all the ionic species in the solution with a charge opposite to that of the desired ion for a single ionic species.

In another embodiment, the reagent is an ion exchange resin which does exchange all of the ionic species in the solution with a charge opposite to that of the desired ion for a single ionic species which then combines with the desired ionic species to form a precipitate resulting in the precipitation of all the desired ionic species from the solution. A subsequent ion exchange step as in the previous embodiment is unnecessary as the solution can be passed directly in contact with the ion specific electrode if an ion specific electrode corresponding to the single ionic species is available, e.g., commercially.

In another embodiment of this invention, the concentration of a specific anion in the solution is determined employing ion exchange resins in the cationic form and cationic specific electrodes.

In another embodiment, the invention provides for the determination of the concentration of a specific cation of the solution by employing ion exchange resins in the anonic form and anion specific electrodes.

DETAILED DESCRIPTION OF THE INVENTION

The present invention provides a novel apparatus setup and method for determining the concentration of an ion in solution. The solution to be analyzed is first divided into a first and second portion. The first portion is treated with a first ion exchange resin in an ion exchange zone which exchanges all of the ionic species in the solution with a charge opposite to that of the desired ion for a single ionic species. The resultant solution is then passed in contact with a first ion specific electrode which is specific to said single ionic species or any ionic species for which said ions of the single ionic species have subsequently been exchanged. In other words, the ion specific electrode is specific for the single ionic species obtained from the exchange in the first ion exchange zone or any ionic species for which the ions of said single ionic species have been exchanged in a subsequent ion exchange zone.

The second portion of the solution is contacted with a reagent that is capable of reacting with the desired ion to give a substantially non-ionic product without substantial reaction with other ions in the solution. The reagent can be a precipitation agent which results in the precipitation of all the desired ionic species from the solution or an agent which combines with the desired ions to form a product which would not be detected by an ion specific electrode. The precipitation agent can be either a reagent which produces cations and anions in the solution or an ion exchange resin.

When the precipitation agent produces cations and anions in solution, either the cationic or anionic species, depending upon whether the desired ion is a cation or anion, combine with the desired ionic species to precipitate and thereby remove all of the desired ionic species from the solution.

Once the second portion of the solution has been treated with the precipitation reagent, the resulting solution is then treated with an ion exchange resin which exchanges all the ionic species in the solution with a charge opposite to that of the desired ion for a single ionic species. Said single ionic species is chosen such that the cationic or anionic species produced by the precipitation reagent which have charge the same as the desired ion and which did not combine with any ionic species in the precipitation zone, would then combine with the single ionic species to form a compound which is not detectable by the second ion specific electrode. It is preferred that a precipitation reagent is employed in the precipitation zone which produces acidic or basic ions in the solution and that an ion exchange resin in the acid or basic form is employed. This would result in the combining of the acidic or basic single ionic species obtained from the ion exchange step with the acidic or basic ions obtained from the precipitation zone to form water. The net result is an imbalance in the concentration of ions between the first solution and the second solution equal to the concentration of the desired ion. The imbalance can then be measured.

When the reagent is an ion exchange resin, the resin exchanges the ionic species in the solution with a charge opposite to that of the desired ion for a single ionic species which is capable of combining with the desired ionic species to form a precipitate. The ion exchange resin exchanges a sufficient amount of ionic species to result in the precipitation of all the desired ionic species from the solution.

A subsequent ion exchange resin can then be employed to exchange all of the ionic species in the solution with a charge opposite to that of the desired ion for a single ionic species. The amount of said single ionic species can be detected or measured by bringing the solution in contact with an ion specific electrode. If the ion exchange resin employed as reagent exchanges all of the ionic species in the solution with a charge opposite to that of the desired ion for a single ionic species capable of combining with the desired ionic species to form a precipitate and thereby result in the precipitation of all the desired ionic species from the solution, a subsequent ion exchange would not be necessary as the solution can be passed directly into contact with an appropriate ion specific electrode as an imbalance in the concentration of ions between the first and second solution equal to the concentration of desired ion has then been obtained. However, if the single ionic species to which the ions with a charge opposite to the desired ion is exchanged by the ion exchange resin is a form for which an appropriate, e.g., commercially available, ion specific electrode is not available, a subsequent ion exchange can still be employed in order to place the ions in a form for which an appropriate ion specific electrode is available.

The reagent can also be an ionic exchange resin which is not a precipitation agent, but an ion exchange resin which exchanges the ionic species in the solution with a charge opposite to that of the desired ion for a single ionic species which can form, in general, a nonionic product which would not be detected by an ion specific electrode upon combining with the desired ion. As with the precipitation agent, the ion exchange resin can exchange all of the ions with a charge opposite to that of the desired ion or an amount sufficient to combine with all of the desired ion. Again, as in the case when the ion exchange resin results in the precipitation of the desired ion, a subsequent ion exchange step may or may not be employed.

The removal of the desired ionic species is governed by equilibrium principle. It is to be noted that the ion exchange resins work based on equilibrium principles and that when reference is made to exchanging all of an ionic species it is intended that all of the ionic species are exchanged which can be, taking into account the equilibrium principles for the specific environment in which the exchange is taking place. The word all is not meant to be used in an absolute sense when discussing ion exchange resins, formation of non-ionic products, and precipitates.

Once all of the desired ions, whose concentration is to be determined, have been combined and/or removed from the solution and all the ionic species with a charge opposite to the desired ion have been exchanged for single ionic species, the second portion of solution is then passed in contact with a second ion specific electrode which is specific to the single ionic species or any ionic species for which the ions of said single ionic species have been exchanged. The second ion specific electrode is connected to the first ion specific electrode through a bridge circuit. Contact of the two solutions with the respective ion specific electrodes, therefore, would result in the measurement of any imbalance in electrical potential between the electrodes, which is proportional to the imbalance in ion concentration between the two solutions, and which is proportional to the desired ion concentration in the solution.

The invention, in other words, involves a first ion removal step in which the desired ions, i.e. those to be measured, are removed from the second stream. This is done by adding a reagent to the second stream providing "reacting" ions and oppositely charged "remaining" ions. All desired ions combine with "reacting" ions to form a non-ionic product. Then in a second ion removal step all ions of the same charge as the reacting ions are replaced by one ionic species. The ions of this one ionic species combine with all "remaining" ions to form a non-ionic product. Now the total ion content of the second stream is reduced as compared to the first stream in an amount equivalent to the content of the desired ions. The second ion specific electrodes (after an eventual further ion exchange) therefore "sees" only this reduced ion concentration.

Whether the ion exchange resins are in the anionic or cationic form and the ion specific electrodes are specific to anions or cations depends upon whether the desired ion whose concentration is being measured is a cation or anion respectively. This can be better understood by explaining the invention in reference to the FIGURE, first with respect to the desired ion being an anion and then with the desired ion being a cation. The FIGURE is also discussed in terms of the reagent being a precipitating agent, the preferred embodiment of this invention, however, this is not meant to be unduly limiting to the invention.

According to one embodiment of the invention, and referring now to the FIGURE, an aqueous solution containing an anionic species (hereinafter referred to as generalized species $A^-$) for which the concentration is desired to be known is transported via conduit 1 to dividing point 2 where the solution is divided into two portions. The reference portion of the solution proceeds through conduit 3 to exchange zone 4 which contains an ion exchange resin in the cationic form. In exchange zone 4 all catonic species in the solution are converted to the specific cation corresponding to the original form of the ion exchange resin. The exchanged reference portion of the solution then proceeds through conduit 5 to the reference side of detector cell 6 which contains reference ion specific electrode 7. Detector cell 6 also contains sample ion specific electrode 8. Ion specific electrodes 7 and 8 are connected to each other through a bridge circuit which measures any imbalance in electrical potential between the electrodes. Reference electrode 7 is specific to the cation corresponding to the original form of the ion exchange resin in exchange zone 4.

From dividing point 2, the sample portion of the solution passes through conduit 9 to precipitation zone 10 to which is also added an excess (compared to $A^-$ concentration) of precipitating agent through conduit 11. Actually an excess of precipitating agent, or any type of reagent, is not required as only an equivalent amount of reagent is necessary. Since the equivalent amount is unknown, however, an excess amount is added to insure that sufficient reagent is added to combine and remove all of the desired ions. The precipitating agent selectively removes $A^-$ from the solution through formation of a compound of $A^-$ which is insoluble (or very slightly soluble) in water. The $A^-$ containing precipitate is separated from the solution and removed via conduit 12. The supernatant phase from precipitation zone 10 proceeds through conduit 13 to exchange zone 14 which contains ion exchange resin in the acid form. In exchange zone 14, all cations in the supernatant phase (those cations present in the original solution plus those resulting from excess precipitating agent) from precipitation zone 10 are converted to hydrogen ions and any basic anions present are neutralized by the hydrogen ions. The acidic solution from exchange zone 14 then passes through conduit 15 to the sample side of detector cell 6 which contains a sample ion specific electrode 8 which in this case is specific to the hydrogen ion.

Optionally in the FIGURE, the acidic solution from exchange zone 14 passes via conduit 16 to exchange zone 17 which contains ion exchange resin in the cation (other than hydrogen ion) form. In exchange zone 17, all hydrogen ions are exchanged for another cation corresponding to the original form of the ion exchange resin in 17. The thus-exchanged solution, containing a single cationic species other than hydrogen, passes through conduit 18 to the sample side of detector cell 6. Detector cell 6 contains sample ion specific electrode 8, which in this case is specific to the cation corresponding to the original form of ion exchange resin in exchange zone 17.

Thus, in this embodiment of the invention, the bridge circuit in detector cell 6 measures the imbalance between the cation concentration in the exchanged reference portion of the solution and the cation concentration of the exchanged sample portion of the solution. That measured imbalance corresponds to the concentration of desired ionic species $A^-$ in the original solution.

Reference ion specific electrode 7 and sample ion specific electrode 8 can be specific to the same cation or to two different cations. If the electrodes are specific to two different cations, it will be necessary to calibrate the response of the electrodes to solutions of known concentrations of the specified cations in order to determine a sensitivity factor to be employed in converting the measured imbalance into actual concentration of $A^-$. If electrodes specific to the same cation are employed in the detector cell, it is also desirable to calibrate the response of the electrodes to solutions o known concentrations of the specified cation in order to determine whether differences exist between the electrodes, whether a sensitivity factor is needed and, if so, what the magnitude of the factor is.

Ion specific electrodes which are specific to a number of cations are currently commercially available. Among the common cation specific electrodes are those capable of measuring hydrogen ion and sodium ion concentration.

The anions which are capable of being determined according to this embodiment of the invention are selected from a wide variety of anoins bearing single or multiple charges. Exemplary of the more common anions frequently observed in aqueous solutions, such as contaminated natural streams and effluents from various industrial plants and processes, are chloride, bromide, iodide, carbonate, sulfate, sulfite, sulfide, phosphate, phosphite, and cyanide. Such anions can be present in the aqueous solutions employed in the present invention alone or in any combinations which do not interfere with the inventive determination.

The precipitating agent employed in precipitation zone 10 (FIGURE) can be any appropriate agent which will result in the precipitation of all of $A^{31}$, however, the most preferred agents can be selected from a broad group of metal ion exchange resins or metal hydroxides, the metal or cation portion of each of which is known to form an insoluble or slightly soluble salt with the anion for which the concentration value is desired. Exemplary common metal ions which form such salts include calcium, barium, iron, cobalt, nickel, copper, zince, silver, cadmium, mercury, lead, tin, and the like. It will be recognized by one skilled in the art that certain of the above-listed cations will form insoluble or slightly soluble salts with certain of the above-listed anions while other combinations will form water-soluble salts and thus will not be useful. Thus, a knowledge of the solubility of a certain salt is necessary for one to know which cation(s) will form an insoluble or slightly soluble salt with the desired anion. Such solubility information is readily available in many published handbooks and textbooks. For example, barium ion forms a slightly soluble salt with sulfate ion, i.e., barium sulfate; whereas barium chloride is quite soluble in water. Silver ion, on the other hand, forms slightly soluble salts with both chloride ion and sulfate ion. Thus, it will be necessary for one to select the appropriate cation which will selectively precipitate the desired anion(s), even in the presence of other anions, if such are present.

Precipitation zone 10 can be selected from several different configurations. It can consist of a bed of solid metal hydroxide of limited solubility in water or metal ion exchange resin in which the metal species is the desired cation for preparation of $A^-$ and through which the sample portion of the stream flows. The precipitation zone can also be a reactor containing the sample portion of the solution and suitable agitation means to which is added excess solid metal hydroxide, excess metal ion exchange resin or an aqueous solution or dispersion of these.

When precipitation zone 10 is a bed of solid metal hydroxide or a metal ion exchange resin, the insoluble or slightly soluble salt accumulates in the bed which must then be removed periodically, e.g., through conduit 12 and regenerated by appropriate means. When precipitation zone 10 is a reactor as described above, the insoluble or slightly soluble salt can be removed through 12, e.g., by decantation or filtration.

The metal ion exchange resin useful as a precipitating agent can be any of the well-known cation exchange resins suitably treated to replace the original cations with the desired cation for precipitation. Such cation exchange resins include the well-knwon sulfonated styrene/divinylbenzene copolymer. The metal ion exchange resin containing the desired cation can be easily prepared by passing through the resin an aqueous solution of a soluble salt of the desired metal, e.g., barium chloride, silver nitrate, zinc chloride, copper sulfate, and the like.

It is preferred to employ in the precipitation zone solid metal hydroxide or metal ion exchange resin so that the finally measured difference in cation concentrations of the treated sample portion of the solution will correspond directly to the original concentration of the desired anion. Of course, it will be recognized that aqueous solutions or slurries of metal hydroxides can be easily added to precipitation zone 10; however, the volume of water added to zone 10 will dilute the treated sample stream and hence, must be considered in calculating the desired anion concentration from the difference in cation concentrations of the two portions of the solution in detector 6. Furthermore, the hydroxides of suitable metals are frequently sparingly soluble in water, thereby necessitating the addition of large amounts of aqueous solution to precipitation zone 10 in order to provide the required excess precipitating agent.

It is, of course, necessary that the solid metal hydroxide in precipitation zone 10 be of sufficient solubility in water to provide enough metal cations to precipitate substantially all the desired anions from the sample portion of the stream. It is also necessary, of course, that the metal ions of the metal ion exchange resin be readily accessible for reaction with the desired anions to form an insoluble or slightly soluble salt. Thus, metal ions needed for precipitation which are too tightly bound to be replaced from the polymeric matrix of the ion exchange resin are not suitable.

The ion exchange resins in exchange zones 4, 14, and 17 can be selected from the well-known cation exchange resins, such as sulfonated styrene/divinylbenzene copolymer.

When metal hydroxides, either aqueous solution or solid, are employed in precipitation zone 10, the ion exchange resin in exchange zone 14 will be in the acid form. The hydroxide anions will, therefore, combine with the hydrogen ions obtained from the exchange zone to form water.

When metal ion exchange resins are employed in precipitation zone 10, the ion exchange resin in exchange zone 14 can be in the acid (hydrogen ion) form or in the form of any suitable metal cation to which the electrode in the sample side of detector 6 is sensitive.

The ion exchange resin in exchange zone 4 can be in the acid (hydrogen ion) form or in the form of any suitable metal cation to which the electrode in the reference side of detector 6 is sensitive. When the ion exchange resin in exchange zone 14 is in the acid form and sample ion specific electrode 8 is specific to a metal cation, optional exchange zone 17 can then be employed with the ion exchange resin in the metal cation form corresponding to the sample ion specific electrode.

It is also within the scope of this embodiment of the invention to determine the concentration of a combination of anions in the original solution. It will be readily apparent to one skilled in the art that by appropriate selection of the precipitating agent, especially the cation moiety thereof, each of the desired anions can be simultaneously precipitated and thus, the total concentration of those anions can be determined.

In another embodiment of the invention, the concentration of a cation or combination of cations in an aqueous solution can be determined.

Referring now to the FIGURE, a description follows which is analogous to that given above for determination of anionic species except that the embodiment of the invention pertaining to determination of cationic species is described.

The aqueous solution containing the cationic species (hereinafter referred to as generalized cation $M^+$) for which the concentration is desired to be known is transported via conduit 1 to dividing point 2 where the solution is divided into two portions. The reference portion of the solution proceeds through conduit 3 to exchange zone 4 which contains an ion exchange resin in the anionic form. In exchange zone 4 all anionic species in the solution are converted to the specific anion corresponding to the original form of the ion exchange resin. The exchanged reference portion of the solution then proceeds through conduit 5 to the reference side of detector cell 6 which contains reference ion specific electrode 7. Detector cell 6 also contains sample ion specific electrode 8. Ion specific electrodes 7 and 8 are connected to each other through a bridge circuit. Reference electrode 7 is specific to the anion corresponding to the original form of the ion exchange resin in exchange zone 4.

From dividing point 2, the sample portion of the solution passes through conduit 9 to precipitation zone 10 to which is also added an excess (compared to $M^+$ concentration) of precipitating agent through conduit 11. The precipitating agent selectively removes M+ from the solution through formation of a compound of M+ which is insoluble (or slightly soluble) in water. The M+ containing precipitate is separated from the solution and removed via conduit 12. The supernatant phase from precipitation zone 10 proceeds through conduit 13 to exchange zone 14 which contains ion exchange resin in the base form. In exchange zone 14 all anions remaining in the supernatant phase (those anions present in the original solution plus those resulting from excess precipitating agent) from precipitation zone 10 are converted to hydroxide ions and any acidic cations present are neutralized. The basic solution from exchange zone 14 then passes through conduit 15 to the sample side of detector cell 6 which contains sample ion specific electrode 8 which in this case is specific to hydroxide ion (or hydrogen ion since hydroxide ion concentration and hydrogen ion concentration are related through the water dissociation constant).

Optionally in the FIGURE, the basic solution from exchange zone 14 passes through conduit 16 to exchange zone 17 which contains ion exchange resin in the anion (other than hydroxide ion) form. In exchange zone 17 all hydroxide ions are exchanged for another anion corresponding to the original form of the ion exchange resin in 17. The thus-exchanged solution containing a single anionic species other than hydroxide passes through conduit 18 to the sample side of detector cell 6 which contains sample ion specific electrode 8 which in this case is specific to the anion corresponding to the original form of ion exchange resin in exchange zone 17.

Thus in this embodiment of the invention, the bridge circuit in detector cell 6 measures the imbalance between the anion concentration in the exchanged reference portion of the solution and the anion concentration of the sample portion of the solution which has been treated with a precipitating agent then with ion exchange resin(s). That measured imbalance corresponds to the concentration of desired cationic species M+ in the original solution.

As described above for the anion determining embodiment, reference ion specific electrode 7 and sample ion specific electrode 8 can be specific to the same anion or to two different anions. As also described in detail above, it may be necessary to calibrate the electrodes to determine whether a sensitivity factor should be applied to convert the measured imbalance into actual concentration of M+ and the magnitude of that factor.

Ion specific electrodes which are specific to a number of anions are also currently commercially available. A particularly useful model is currently available which is capable of measuring fluoride ion concentration. Of course, many electrodes are commercially available for determining hydroxide (or hydrogen) ion concentration.

The cations which are capable of being determined, according to this embodiment of the invention, are selected from a wide variety of cations bearing single or multiple charges. Exemplary of the more common cations frequently observed in aqueous solutions, such as contaminated natural streams and effluents from various industrial plants and processes, are potassium, calcium, barium, iron, copper, nickel, zinc, silver, mercury, tin, lead, and the like. Such cations can be present in the aqueous solutions employed in this embodiment of the invention alone or in any combinations which do not interfere with the inventive determination of the desired cation(s).

It is also within the scope of the invention to determine the concentration of a combination of cations in the original aqueous solution. Selection of an apprpriate precipitating agent which will simultaneously precipitate each of the desired cations will result in the measured imbalance in the detector cell being proportional to the sum of the concentrations of each of the desired cations.

The precipitating agent employed in precipitation zone 10 of this embodiment can be selected from a wide range of anion exchange resins and mineral acies or organic acids, the anion portion of each of which is known to form an insoluble or slightly soluble salt with the cation(s) for which the concentation is desired. Exemplary common anions available from anion exchange resins or acids include chloride, bromide, sulfate, carbonate, sulfide, oxalate, tartrate, and the like. It will be recognized by one skilled in the art that certain of these anions will form insoluble or slightly soluble salts with certain of the desired cations while other combinations will form water-soluble salts and thus will not be useful. Thus a knowledge of the solubility of a certain salt is necessary for one to select the anion which will be effective in precipitating the desired cation. Such solubility information is readily available in many published handbooks and textbooks. For example, potassium ion forms a slightly soluble salt with tartaric acid, potassium hydrogen tartrate, whereas potassium sulfate and potassium chloride are quite soluble in water. Barium ion, on the other hand, forms a soluble salt with chloride but a slightly soluble salt with sulfate. Thus, in this embodiment of the invention, it will be necessary for one to carefully select the appropriate anion which will selectively precipitate the desired cation(s), even in the presence of other cations.

The above description of the various configurations possible for the precipitation zone 10 for the first embodiment of the invention is also applicable for this embodiment when one employs suitable anion exchange resins or acids as precipitating agent.

The anion exchange resin useful as a precipitating agent in this embodiment of the invention can be any of the well-known anion exchange resins suitably treated to replace the original anions with the desired anion for precipitation. Such anion exchange resins include the well-known styrene/divinylbenzene copolymers containing quaternary ammonium groups along the polymer chains. The anion exchange resins containing the desired anion can be easily prepared by passing through the resin an aqueous solution of a soluble salt of the desired anion.

As described for the embodiment of the invention for determining anion concentration, this embodiment also requires that any water added in the precipitation zone with the precipitating agent be considered in calculating the concentration of the desired cation from the measured imbalance in the detector.

As also described for the embodiment of the invention for determining anion concentration, the anions suitable for precipitation of the desired cations in this embodiment must be available for precipitation, i.e., they must be readily replaceable from the anion exchange resin or must be available in solution from the acids employed.

The ion exchange resins useful in this embodiment of the invention in exchange zones 4, 14, and 17 are selected from the well-known anion exchange resins such as those described above.

When acids, either mineral or organic, are employed in the precipitation zone, the ion exchange resin in exchange zone 10 can be in the hydroxide form. When anion exchange resins are employed in precipitation zone 10, the ion exchange resin in exchange zone 14 can be in either the hydroxide form or in the form of any suitable anion to which electrode 8 in the sample side of detector 6 is sensitive.

When this embodiment of the invention is practiced, the ion exchange resin in exchange zone 4 will be in the hydroxide form or in the form of any suitable anion to which reference electrode 7 in the reference side of detector 6 is sensitive. When the ion exchange resin in exchange zone 14 is in the hydroxide form and sample electrode 8 is specific to a different anion than hydroxide, then optional exchange zone 17 can be employed with the ion exchange resin in the form corresponding to the anion to which sample electrode 8 is sensitive.

Instead of the ion exchange zone 4 being arranged in the reference stream line it is also within the scope of this invention to provide such an ion exchange zone in the line 1 of the solution to be measured. The basic principle of this invention remains unchanged, the reference electrode sees ions in a quantity equivalent to the concentration of the original solution whereas the measurement electrode sees ions in a concentration that is reduced from the original concentration of the solution by a quantity equivalent to the concentration of the desired ions.

The following example is a calculated example which is intended to illustrate the invention without any undue limitation thereof.

EXAMPLE

A feedstream 1 containing a variety of ions of which the sulfate ion concentration is to be determined is split into a measurement portion in line 9 and a reference portion in line 3. The measurement portion is contacted in zone 10 with an aqueous barium hydroxide solution. All sulfate ions in the stream of line 9 are precipitated in the form of barium sulfate in zone 10 and the barium sulfate is withdrawn via line 12 from this zone. Since barium hydroxide in stream 11 has to be used at least in a small excess over the sulfate ion concentration, stream 13 will contain a certain amount of excess barium ions and an equivalent amount of excess hydroxyl ions. In the ion exchanger 14 all cations that are not $H^+$ are replaced by $H^+$ ions. Thus, the quantity of $H^+$ ions corresponding to the barium ions having entered ion exchange zone 14 will combine with all of the excess hydroxyl ions to form neutral water molecules. Stream 15 therefore contains hydrogen ions in a concentration equivalent to the original ion concentration of stream 1 minus the equivalent concentration of sulfate ions. Electrode 9 therefore sees hydrogen ions of a reduced concentration.

The reference portion in line 3 is ion exchanged in ion exchange zone 4 by replacing all the cations by hydrogen ions ($H^+$). Stream 5 is passed to electrode 7 so that electrode 7 sees a liquid having an $H^+$ concentration equivalent to the total cation concentration in stream 1.

The difference in electrical potential between the two electrodes 7 and 8 is therefore directly representative of the concentration of sulfate ions in stream 1.

All of the embodiments of the invention are readily adaptable to either batch or continuous operation.

Reasonable variations and modifications which will become apparent to those skilled in the art can be made in the present invention without departing from the spirit and scope thereof.

I claim:

1. A method for measuring the concentration of a desired ion in a solution comprising the steps of:
   (a) dividing the solution to be analyzed into a first and second portion,
   (b) treating the first portion with a first ion exchange resin which exchanges all of the ionic species in the solution with a charge opposite to that of the desired ion for a single ionic species,
   (c) passing the resultant solution from step (b) in contact with a first ion specific electrode which is specific to the single ionic species of step (b) or any ionic species for which the ions of said single ionic species have been exchanged,
   (d) treating the second portion of solution with a reagent that renders "reacting" ions of one charge and "remaining" ions of the opposite charge in an amount sufficient to provide "reacting" ions for all desired ions,
   (e) combining "reacting" ions and all the desired ions to form a substantially non-ionic product without substantial reaction with other ions in the solution,
   (f) treating the resultant solution from step (e) with a second ion exchange resin which exchanges all of the ionic species in said resultant solution with a charge opposite to that of the desired ion for a single ionic species which combines with all of the "remaining" ions to thereby form a compound not detectible by a second ion specific electrode,
   (g) passing the resulting solution of step (f) in contact with a second ion specific electrode which is specific to the single ionic species of step (f) or any ionic species for which the ions of said single ionic species have been exchanged and said electrode is connected to the first ion specific electrode through a circuit which measures any imbalance in electrical potential between the electrodes, and
   (h) determining the concentration of the desired ion from the difference in electrical potential between said first and said second ion specific electrodes.

2. The method of claim 1 wherein the reagent of (d) is a precipitation agent which yields a precipitate as the non-ionic product of (e) resulting in the precipitation of all the desired ionic species from the solution.

3. The method of claim 2 wherein the desired ion is an anion,
   the first and second ion exchange resins are in the cationic form, and
   the ion specific electrodes are cation specific.

4. The method of claim 2 wherein the desired ion is a cation,
   the first and second ion exchange resins are in an anionic form, and
   the ion specific electrodes are anion specific.

5. The method of claim 2 wherein the resulting solution from step (f) is first passed to a third ion exchange resin to thereby exchange all of the ions of the single ionic species of step (f) for a different ionic species to which said second ion specific electrode is specific.

6. The method of claim 2 wherein said first and second ion specific electrodes are specific to the same ionic species.

7. The method of claim 3 wherein the cation specific electrodes are selected from the group consisting of those electrodes which are capable of measuring hydrogen ion or sodium ion concentrations and the ion exchange resins are in a form which exchange all cations for either the hydrogen or sodium ion.

8. The method of claim 3 wherein the anion to be measured is selected from the group consisting of chloride, bromide, iodide, carbonate, sulfate, sulfite, sulfide, phosphate, phosphite and cyanide.

9. The method of claim 4 wherein the anion specific electrodes are selected from the group consisting of those electrodes which are capable of measuring fluoride or hydroxide ion concentrations and the ion exchange resins are selected from the group consisting of those ion exchange resins which are capable of exchanging all anions to fluoride or hydroxide ions.

10. The method of claim 4 wherein the cation to be measured is selected from the group consisting of potassium, calcium, barium, iron, copper, nickel, zinc, silver, mercury, tin and lead.

11. The method of claim 5 wherein the desired ion is an anion,
the first ion exchange resin is capable of exchanging all cations for either the hydrogen or sodium ion,
the second ion exchange resin is capable of exchanging all cations for the hydrogen ion, and
the third ion exchange resin is capable of exchanging all hydrogen ions for sodium ions.

12. The method of claim 5 wherein the desired ion is a cation,
the first ion exchange resin is capable of exchanging all anions for the hydroxide or fluoride ion,
the second ion exchange resin is capable of exchanging all anions for the hydroxide ion, and
the third ion exchange resin is capable of exchanging all hydroxide ions for the fluoride ion.

13. The method of claim 2 wherein the desired ion is an anion,
said precipitation agent is an hydroxide compound, and
said second ion exchange resin is capable of exchanging all cations for hydrogen ions thereby resulting in the hydrogen ions combining with the hydroxide ions obtained from the precipitation agent to form water.

14. The method of claim 2 wherein said desired ion is a cation,
said precipitation agent is a compound which will form hydrogen ions upon dissolving in the solution, and
said second ion exchange resin exchanges all of the anions in the solution for hydroxide ions thereby resulting in the combination of said hydroxide ions with the hydrogen ions of the precipitating agent to form water.

15. A method for measuring the concentration of a desired ion in a solution comprising the steps of:
(a) dividing the solution to be analyzed into a first and second portion,
(b) treating the first portion with a first ion exchange resin which exchanges all of the ionic species in the solution with a charge opposite to that of the desired ion for a single ionic species,
(c) passing the resultant solution from step (b) in contact with a first ion specific electrode which is specific to the single ionic species of step (b) or any ionic species for which the ions of said single ionic species have been exchanged,
(d) treating the second portion of solution with a second ion exchange resin which exchanges all of the ionic species in the solution with a charge opposite to that of the desired ion for a single ionic species which then combine with the desired ions to form a substantially non-ionic product without substantial reaction with other ions in solution,
(e) passing the resulting solution of step (d) in contact with a second ion specific electrode which is specific to the single ionic species of step (d) or any ionic species for which the ions of said single ionic species have been exchanged and said electrode is connected to the first ion specific electrode through a circuit which measures any imbalance in electrical potential between the electrodes, and
(f) determining the concentration of the desired ion from the difference in electrical potential between said first and said second ion specific electrodes.

16. A method for measuring the concentration of a desired ion in a solution comprising the steps of:
(a) dividing the solution to be analyzed into a first and second portion,
(b) treating the first portion with a first ion exchange resin which exchanges all of the ionic species in the solution with a charge opposite to that of the desired ion for a single ionic species,
(c) passing the resultant solution from step (b) in contact with a first ion specific electrode which is specific to the single ionic species of step (b) or any ionic species for which the ions of said single ionic species have been exchanged,
(d) treating the second portion of solution with a second ion exchange resin which exchanges the ionic species in the solution with a charge opposite to that of the desired ion for a single ionic species which then combines with the desired ionic species to form a substantially non-ionic product without substantial reaction with other ions in solution wherein said ion exchange resin exchanges a sufficient amount of the ionic species to result in the combination of all of said desired ionic species to form a substantially non-ionic product,
(e) treating the resultant solution of step (d) with a third ion exchange resin which exchanges all of the ionic species in said resultant solution with a charge opposite to that of the desired ion for a single ionic species,
(f) passing the resulting solution of step (e) in contact with a second ion specific electrode which is specific to the single ionic species of step (e) or any ionic species for which the ions of said single ionic species have been exchanged and said electrode is connected to the first ion specific electrode through a bridge circuit which measures any imbalance in electrical potential between the electrodes, and
(g) determining the concentration of the desired ion from the difference in electrical potential between said first and said second ion specific electrodes.

17. The method of claim 15 or claim 16 wherein the non-ionic product formed is a precipitate thereby resulting in the precipitation of all the desired ionic species from the solution.

18. The method of claim 17 wherein the desired ion is an anion,
the first and second ion exchange resins are in the cationic form, and
the ion specific electrodes are cation specific.

19. The method of claim 17 wherein the desired ion is a cation,
the first and second ion exchange resins are in an anionic form, and
the ion specific electrodes are anion specific.

20. The method of claim 15 wherein the resulting solution from step (d) is passed to a third ion exchange resin to thereby exchange all of the remaining ions of the single ionic species of step (d) for a different ionic species to which said second ion specific electrode is specific and the solution so obtained is passed in contact with said second ion specific electrode.

21. The method of claim 15 wherein the desired ion is an anion and said second ion exchange resin is a metal ion exchange resin.

22. An apparatus useful in measuring the ion concentration of a desired ion in a solution comprising,
means for splitting said solution into a first and second portion,
means defining a precipitation zone having means for receiving one of the portions of said solution and means for removing the desired ion from solution,
means defining at least a first and second ion exchange zone comprising an ion exchange resin which is capable of exchanging the ionic species in the solution contacted therewith which have a charge opposite to that of the desired ion for a single ionic species,
a detection means comprising a first and second ion specific electrode connected to a bridge circuit for detecting the difference in electrical potential between the two ion specific electrodes,
conduit means for passing the first portion of said solution to the first ion exchange zone and the second portion of said solution to the precipitation zone,
conduit means connecting said first ion exchange zone to the detection means with access to the first ion specific electrode which is specific to the single ionic species in that portion of the solution, and
conduit means for passing the solution from the precipitation zone to the second ion exchange zone and then connecting said second ion exchange zone to the detection means with access to the second ion specific electrode which is ion specific to the single ionic species in that portion of the solution.

23. The apparatus of claim 22 which further comprises means defining a third ion exchange zone which is connected by conduit means to the second ion exchange zone and the detection means with access to the second ion specific electrode wherein said third ion exchange zone comprises an ion exchange resin which exchanges the ionic species in the solution contacted therewith having a charge opposite to the desired ion for a single ionic species to which the second ion specific electrode is specific.

24. The apparatus of claim 22 wherein the ion specific electrodes are cation specific and the ion exchange resins in the ion exchange zones are in the cationic form.

25. The apparatus of claim 22 wherein the ion specific electrodes are anion specific and the ion exchange resins and the ion exchange zones are in the anionic form.

26. The apparatus of claim 22 wherein the ion specific electrodes are specific to the same ionic species.

27. The apparatus of claim 24 wherein the ion specific electrodes are specific to the hydrogen ion or the sodium ion and the ion exchange resins are capable of exchanging cations in the solution for hydrogen or sodium ions.

28. The apparatus of claim 25 wherein the ion specific electrodes are specific to the fluoride or hydroxide ion and the ion exchange resins are capable of exchanging anions for fluoride or hydroxide ions.

29. Method for measuring the concentration of desired ions in a solution, said solution containing first feed ions of a first charge in an initial concentration, second feed ions of a second charge opposite to the first charge in an equivalent concentration and containing among the first feed ions the desired ions to be measured, said method comprising,
(a) generating a reference stream from said solution containing only such ions in one charge to which a reference electrode is sensitive, and containing these ions in a concentration equivalent to said initial concentration,
(b) passing this reference stream into contact with said reference electrode,
(c) generating a measurement stream from said solution,
(d) converting the desired ions of said measurement stream to a non-ionic product and leaving an intermediate measurement stream having an ion concentration equivalent to the difference of the initial ion concentration minus the concentration of said desired ions and deriving a final measurement stream from the intermediate measurement stream such that the final measurement stream contains only such ions of one charge to which a measurement electrode is sensitive,
(e) passing the final measurement stream derived from the intermediate measurement stream of step (d) and containing only such ions of one charge to which a measurement electrode is sensitive and containing these ions in a concentration equivalent to the initial ion concentration minus the concentration of said desired ions, into contact with said measurement electrode, and
(f) determining the relative electrical potential between the measurement electrode and the reference electrode.

30. Method in accordance with claim 29 comprising
(a) passing said solution through an ion exchange resin such as to generate a solution stream containing only such ions of said second charge to which said reference electrode is sensitive,
(b) passing a reference portion of said solution stream as said reference stream into contact with said reference electrode, and
(c) generating said measurement stream as a portion of said solution having passed through said ion exchange resin.

31. Method in accordance with claim 29 comprising
(1) dividing said solution into a reference portion and a measurement portion,
(2) using said measurement portion as said measurement stream,
(3) passing said reference portion of said solution into contact with an ion exchange resin which exchanges all ions of one charge and replaces them by ions of the same charge to which said reference electrode is sensitive, and
(4) using the so ion exchange stream as said reference stream.

32. Method in accordance with claim 31 comprising exchanging all second feed ions of the second charge in said reference portion by a single ionic species.

33. Method in accordance with claim 31 or 32, with steps (d) and (e) comprising
   (a) contacting in a precipitation zone said measurement portion with a reagent containing reagent ions of a first charge and reagent ions of a second charge in a quantity exceeding the concentration of said desired ions in said measurement portion, said reagent ions of said second charge being capable of reacting essentially only with said desired ions and not with other ions of the first charge in said measurement portion, thereby producing a non-ionic product from all desired ions and an equivalent amount of reagent ions of the second charge,
   (b) withdrawing from said precipitation zone a liquid intermediate stream containing excess reagent ions of said first charge and an equivalent amount of excess reagent ions of said second charge,
   (c) contacting said intermediate stream with an ion exchange resin to replace ions of one charge including the excess reagent ions by neutralizing ions which combine with excess reagent ions of the other charge but not with other kinds of ions of the other charge to form a non-ionic product, and
   (d) passing the so-treated intermediate stream having an ion concentration equivalent to the initial concentration minus the concentration of the desired ions after an optional further ion exchange step into contact with said measurement electrode.

34. Method in accordance with claim 30 or 31, with steps (d) and (e) comprising
   (a) contacting said measurement portion with an ion exchange resin which exchanges the ionic species in the solution with a charge opposite to that of the desired ion for a single ionic species which then combines with the desired ionic species to form a substantially non-ionic product without substantial reaction with other ions in the solution, with the proviso that said ion exchange resin exchanges a sufficient amount of the ionic species to result in a combination of all of said desired ionic species to form said substantially non-ionic product,
   (b) contacting the measurement stream from step (a) with a further ion exchange resin which exchanges all of the ionic species in this stream having a charge opposite to that of the desired ion for a single ionic species,
   (c) passing the resulting stream from step (b) optionally after another ion exchange treatment as said final measurement stream to said measurement electrode.

35. Method in accordance with claim 29 wherein said measurement electrode and said reference electrode are sensitive to ions of the same charge.

36. Apparatus for measuring the ion concentration of a desired ion in a solution comprising
   (a) means defining a source of said solution,
   (b) first means to convert at least a first portion of said solution into a reference stream containing only such ions of one charge in a concentration equivalent to the initial concentration of said solution, to which ions a reference electrode is sensitive,
   (c) second means for converting a second portion of said solution into a final measurement stream containing only such ions of the same charge as the charge mentioned in (b) to which ions a measurement electrode is sensitive, in a concentration equivalent to said initial concentration minus the concentration of said desired ions, said second means comprising non-ionic product generating means for converting said desired ions into a non-ionic product,
   (d) conduit means connecting said source of said solution to said first and said second means,
   (e) a measurement electrode sensitive to the specific ions of (c)
   (f) a reference electrode sensitive to the specific ions of (b)
   (g) measurement conduit means connecting said first means with said reference electrode,
   (h) reference conduit means connecting said second means with said measurement electrode,
   (i) potential detector means attached to said electrodes capable of detecting the electric potential between said electrodes and of generating an information signal representative of said electric potential.

* * * * *